United States Patent [19]

Bale Oenick et al.

[11] Patent Number: 5,462,858
[45] Date of Patent: Oct. 31, 1995

[54] DRY MULTILAYER ANALYTICAL ELEMENTS FOR ASSAYING TRANSAMINASES

[75] Inventors: Marsha D. Bale Oenick, Rochester; Richard L. Detwiler, Webster; Jon N. Eikenberry; John W. H. Sutherland, both of Rochester, all of N.Y.

[73] Assignee: Eastman Kodak Company, Rochester, N.Y.

[21] Appl. No.: 175,013

[22] Filed: Dec. 29, 1993

[51] Int. Cl.$^6$ .............................. C12Q 1/52; C12Q 1/26; C12Q 1/28; G01N 21/25
[52] U.S. Cl. .............. 435/16; 435/25; 435/26; 435/805; 422/56; 422/57
[58] Field of Search .................. 435/16, 15, 25, 435/28, 805; 436/169; 428/327, 328, 478.2, 475.2, 331; 422/55, 56, 57

[56] References Cited

U.S. PATENT DOCUMENTS

| | | | |
|---|---|---|---|
| 4,089,747 | 5/1978 | Bruschi | 195/99 |
| 4,246,342 | 1/1981 | Misaki et al. | 435/25 |
| 4,450,232 | 5/1984 | Sanford et al. | 435/15 |
| 4,495,293 | 1/1985 | Shaffar | 436/501 |
| 4,503,145 | 3/1985 | Katsuyama et al. | 435/16 |
| 4,547,465 | 10/1985 | Eikenberry | 436/170 |
| 4,578,245 | 3/1986 | Arai et al. | 422/56 |
| 4,897,347 | 1/1990 | Katsuyama et al. | 435/16 |
| 4,965,194 | 10/1990 | Yamamoto et al. | 435/25 |
| 5,066,462 | 11/1991 | Kawasaki et al. | 432/56 |
| 5,130,258 | 7/1992 | Makino et al. | 436/169 |

FOREIGN PATENT DOCUMENTS

| | | | |
|---|---|---|---|
| 382207A3 | 8/1990 | European Pat. Off. | G01N 33/5 |
| 525550A1 | 2/1993 | European Pat. Off. | G01N 33/5 |
| 62-079362A | 4/1987 | Japan | G01N 31/22 |

Primary Examiner—Paul J. Thibodeau
Assistant Examiner—Vivien Chen

[57] ABSTRACT

A dry multilayer analytical element for assaying transaminases wherein the analytical element comprises:
a) a transaminase substrate;
b) reagents that generate pyruvate in the presence of a transaminase and the transaminase substrate;
c) pyruvate oxidase and cofactors for pyruvate oxidase; and
d) reagents that generate a color in proportion to a concentration of hydrogen peroxide;
and wherein the analytical element has, in the following order, a spreading layer, a reagent layer, and a support wherein
i) the spreading layer contains the transaminase substrate and a material selected from the group consisting of polymer beads, barium sulfate, titanium oxide, and mixtures thereof;
ii) the reagent layer contains the pyruvate oxidase; and
iii) both a hardened gelatin layer and a subbing layer separate the reagent layer from the spreading layer.

14 Claims, No Drawings

DRY MULTILAYER ANALYTICAL ELEMENTS FOR ASSAYING TRANSAMINASES

FIELD OF THE INVENTION

This invention relates to the field of clinical chemistry.

BACKGROUND

Alanine transaminase (ALT), also known as glutamate-pyruvate transaminase (GPT, SGPT), and aspartate transaminase (AST), also known as glutamate-oxaloacetate transaminase (GOT, SGOT), have clinical significance in the diagnosis of disease. Abnormal levels of both transaminases are seen in patients with hepatic disease, myocardial and skeletal muscle necrosis and other diseases.

Methods and multilayer dry elements for assaying both transaminases are known. U.S. Pat. No. 4,897,347 discloses a method and element based on the following chemical reactions:

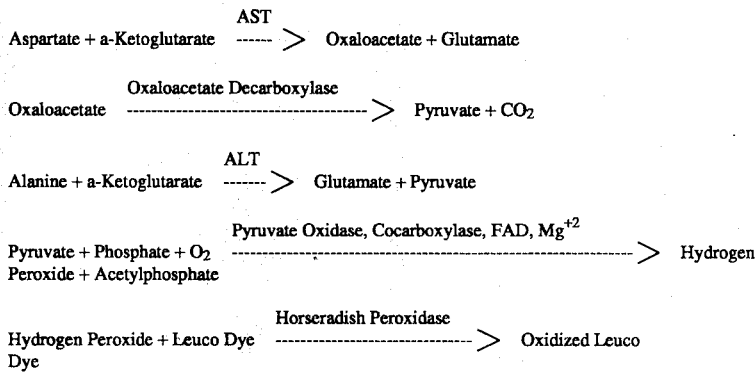

U.S. Pat. No. 4,897,347 requires that the pyruvate oxidase be present in the uppermost porous layer or in a layer adjacent to the uppermost layer. Reference examples 1 and 2 are presented therein. The elements of these examples involve a layer comprising titanium dioxide layer between the uppermost layer and the layer containing the pyruvate oxidase. These examples show such elements are unsatisfactory in that the range of concentrations of transaminase determinable by the elements is narrow with maximum concentration of less than 200 U/l. See FIG. 10 thereof.

The problem is that incorporation of enzymes into spreading layers made from dispersed inorganic compounds or polymeric beads in a manner in which enzymatic activity is retained is difficult and often requires a subsequent coating step to add the enzyme to a preformed spreading layer. Moreover spreading layers generally require a subbing layer between them and underlying reagent layers for adherence. Also pyruvate oxidase is expensive.

SUMMARY OF THE INVENTION

The present invention provides a dry multilayer analytical element for assaying transaminases having, in the following order, a spreading layer, a reagent layer and a support and said element comprises:

a) a transaminase substrate;

b) reagents that generate pyruvate in the presence of a transaminase and the transaminase substrate;

c) pyruvate oxidase and cofactors for pyruvate oxidase;

d) reagents that generate a color in proportion to a concentration of hydrogen peroxide; characterized in that:

e) the spreading layer contains the transaminase substrate and a material selected from the group consisting of polymer beads, barium sulfate, titanium dioxide and mixtures thereof;

f) the reagent layer contains the pyruvate oxidase; and g) at least one layer separates the spreading layer from the reagent layer.

A useful embodiment of the invention is a dry multilayer elements for assaying aspartate aminotransaminase having, in the following order, a spreading layer, a reagent layer and a support and said element comprises:

a) aspartate;

b) reagents that generate pyruvate in the presence of aspartate aminotransaminase and asparate;

c) pyruvate oxidase and cofactors for pyruvate oxidase;

d) reagents that generate a color in proportion to a concentration of hydrogen peroxide; characterized in that:

e) the spreading layer contains the transaminase substrate and a material selected from the group consisting of polymer beads, barium sulfate, titanium dioxide and mixtures thereof;

f) the reagent layer contains the pyruvate oxidase; and g) at least one layer separates the spreading layer from the reagent layer.

Another useful embodiment is a dry multilayer element for assaying alanine aminotransaminase having, in the following order, a spreading layer, a reagent layer and a support and said element comprises:

a) alanine;

b) reagents that generate pyruvate in the presence of alanine aminotransaminase and alanine;

c) pyruvate oxidase and cofactors for pyruvate oxidase;

d) reagents that generate a color in proportion to a concentration of hydrogen peroxide; characterized in that:

e) the spreading layer contains the transaminase substrate and a material selected from the group consisting of polymer beads, barium sulfate, titanium dioxide and mixtures thereof;

f) the reagent layer contains the pyruvate oxidase; and g) at least one layer separates the spreading layer from the reagent layer.

The utility of this element is surprising in view of the teachings of the above U.S. Pat. No. 4,897,347 that the placement of layers between the uppermost layers and the pyruvate oxidase containing layer destroyed the utility of elements. This element allows assay of transaminases colorimetrically using much less pyruvate oxidase than used in the examples of the above U.S. patent. The coating problems mentioned above are avoided.

DETAILS OF THE INVENTION

Spreading layers, including their function and preparation are well known in dry analytical arts. They are described in many patents such as U. S. Pat. No. 4,357,363 and many others. Barium sulfate or titanium dioxide or mixtures thereof are useful spreading layers. Polymer bead spreading layers disclosed in U.S. Pat. No. 4,258,001 can also be used. They are adhered to the various underlayers by a subbing layer. The pyruvate oxidase containing layer can also contain the reagents for generating color in the presence of hydrogen peroxide. The latter reagents may be maintained in a separate layer. In each case, a subbing layer between the spreading layer and the enzyme layers exists. When the pyruvate oxidase containing layer also contains the color generating reagents, avoidance of physical defects and improved precision is provided by the intervening subbing and/or gelatin layers.

The reagents that generate a color in proportion to the concentration of hydrogen peroxide can be a single compound which produces a detectable dye upon enzymatic reaction, or a combination of reagents which produce the dye. The colorimetric indicator composition can include a coupler and oxidizable compound which reacts to provide a dye. Alternatively, the reagents can include a leuco dye and peroxidase, such as horseradish peroxidase or another suitable peroxidative compound, such as horseradish peroxidase, which generate a detectable dye as a result of the presence of hydrogen peroxide. Useful leuco dyes are known in the art and include those, for example, described in U.S. Pat. No. 4,089,747 (issued May 16, 1978 to Bruschi) and U.S. Pat. No. 4,670,385, filed May 21, 1984 by Babb et al.

The function and preparation of subbing layers are well know in this art. The art provides a wide variety of materials for selection of subbing materials. In the examples of the present invention various grades of polyvinylpyrrolidone, based on molecular weight, are used. Other subbing materials include gelatin, other natural colloids, and hydrophilic synthetic polymers such as polyacrylamide, poly(N-isopropylacrylamide) and polymethacrylamide, and other N-substituted acrylamide polymers, and copolymers of a substituted or unsubstituted acrylamide or cyclic amine monomer such as vinylpyrrolidone and vinylimidazole with one or more other hydrophilic monomers such as hydroxyalkyl acrylates and methacrylates, e.g., hydroxyethyl methacrylate, and acrylic and methacrylic acids, and optionally with a polyfunctional crosslinking monomer such as N,N'-methylenebisacrylamide, ethylene diacrylate, divinylebenzene.

The layers can be coated using well known coating techniques in this art. For example slideextrusion hoppers of the type described in U.S. Pat. No. 2,761,417 are often advantageous for simultaneous coating of a plurality of layers.

Transaminases measured with the present invention are those which are specifically described in the classification No. 2.6.1 of Enzyme Nomenclature, 1972 edition, published by Elsevia Co. (1973) approved by International Union of Biochemistry, such as those mentioned under the background of the invention, supra.

An indirect reaction in which pyruvate is produced may be one in which another enzymatic reaction is concerned or may be a non-enzymatic chemical reaction. In any case, any process in which an enzymatic or chemical reaction is used in combination with a transaminase reaction to produce hydrogen peroxide as a final product from pyruvate may be used. Among them, measurement of ALT and AST activities are most important diagnostically.

The substance which is a substrate for the transaminase is only required to have an amino group therein, and since the relationship between a substrate enzyme couple is well known by those in the art, no detailed explanation will be given.

Transaminase is an enzyme which promotes transfer of the amino group in an amino acid to an α-keto acid. The substrate for transaminase includes the amino acid and α-keto acid. Alanine and aspartate are used to illustrate the present invention.

Pyruvate oxidase used in the multilayer analysis film of the present invention is usually activated by a Pyruvate oxidase activator in order to accelerate the reaction. Examples of the pyruvate oxidase activator include coenzymes, inorganic phosphates, bivalent metal ions and the like.

The pyruvate oxidase activator is generally employed in an amount of $10^{-9}$ to $10^{-5}$ mole per unit of pyruvate oxidase.

Typical coenzymes include flavin adenine dinucleotide, cocarboxylase(thiamine pyrophosphate), etc.; typical inorganic phosphates include primary and secondary sodium phosphates, primary and secondary potassium phosphates, etc.; and, typical bivalent metal ions include $Mg^{2+}$, $Mn^{2+}$, $Ca^{2+}$, $Co^{2+}$ and the like. In general the range of concentrations of the various reagents used in the elements of the invention are set according to the range of transaminases observed in patient samples. Such ranges can be set by anyone skilled in the art. In general the ranges can be set according the following table.

| | General Range | Preferred Range |
|---|---|---|
| Peroxidase (U/m$^2$) | 500–100,000 | 1,000–50,000 |
| Substrate (g/m$^2$) | 0.5–500 | 1–150 |
| Leuco dye (g/m$^2$) | 0.01–5 | 0.1–3 |
| Pyruvate oxidase (U/m$^2$) | 200–100,000 | 500–10,000 |
| Oxaloacetate Decarboxylase (U/m$^2$) | 5–100,000 | 10–10,000 |
| Coenzyme (g/m$^2$) | 0.01–10,000 | 0.1–5,000 |

All of the reagents needed to carry out the series of reactions upon which the present assay is based and described under the background of the invention are available commercially.

The element of this invention can be used to assay transaminases qualitatively and quantitatively in biological fluids in animals or humans, but preferably of humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

Elements of the invention can be configured in a variety of forms, including elongated tapes of any desired width, sheets, slides or chips.

The elements can be used in manual or automated assay techniques. In general, in using the elements, analyte determination is made by taking the element from a supply roll, chip packet or other source and physically contacting it with a sample (for example, up to 200 µl, preferably about 10 to 12 µl) of the liquid to be tested so that the sample and reagents become mixed with liquid and interact within the element to produce the sequential reactions necessary to color formation. Such contact can be accomplished in any suitable manner, for example, by dipping or immersing the element into the sample or, preferably, by spotting the element by hand or machine with a drop of the sample with a suitable dispensing means.

After sample application, the element is incubated, for a period of up to 5 minutes, to facilitate color development. By incubation, we simply mean that the reagents are maintained in contact with each other for a period of up to 5 minutes before color measurements are made.

The layers are generally in fluid contact with each other, meaning that fluids, reagents and reaction products (for example, color dyes) can pass or be transported between superposed regions of adjacent zones. In other words, when the element is contacted with an aqueous fluid, all reagents of the analytical composition of this invention are mixed as stated hereinbefore and can readily move within the element as a composition. Each layer can be separate or two or more zones can be separate areas in a single layer of the element. Besides the references noted above, suitable element components are described also, for example, in U.S. Pat. Nos. 4,042,335 (issued Aug. 16, 1977 to Clement), 4,132,528 (issued Jan. 2, 1979 to Eikenberry et al), and 4,144,306 (issued Mar. 13, 1979 to Figueras).

Since the sample is generally applied directly to the spreading layer, it is desirable that the spreading layer be isotropically porous, meaning that the porosity is the same in each direction in the layer as caused by interconnected spaces or pores between particles, fibers or polymeric strands.

The layers can be coated on transparent supports such as polyethylene terephthalate. Other supports are well known in the art. The back of the support may be coated with a dye composition that filters out unwanted radiation.

The elements of this invention can also contain one or more other addenda commonly put in the elements for various manufacturing or operational advantages. Such addenda include surfactants, buffers, solvents, hardeners and other materials known in the art.

EXAMPLES

The following examples illustrate the utility of the present invention.

Example 1

FIG. 1 shows the configurations and compositions of elements of the invention for assaying alanine transaminase (ALT).

| | FIG. 1 | | | |
|---|---|---|---|---|
| | | Coating A g or U/m$^2$* | Coating B g or U/m$^2$* | Coating C g or U/m$^2$* |
| Spreading Layer | Sodium a-Ketoglutarate | 0.54 | 0.54 | 0.54 |
| | Alanine | 8.61 | 8.61 | 8.61 |
| | Barium Sulfate | 93.08 | 93.08 | 93.08 |
| | Cellulose Acetate | 7.87 | 7.87 | 7.87 |
| | Hexadecyl Pyridinium Bromide | 1.07 | 1.07 | 1.07 |
| | TX405 | 1.85 | 1.85 | 1.85 |
| | Estane | 0.93 | 0.93 | 0.93 |
| Subbing Layer | PVPK30 | 1.07 | 1.07 | 1.07 |
| Gelatin Layer | Gelatin | 3 | 6 | 0 |
| | Sodium Hydroxide | 0.0171 | 0.0342 | 0 |
| | TX405 | 0.01 | 0.01 | 0 |
| | Bis(vinylsulfonylmethyl) Ether | 0.06 | 0.12 | 0 |
| | TX200 | 0.004 | 0.004 | 0 |
| Reagent | Gelatin | 8.22 | 8.22 | 8.22 |
| | Tricine | 2.52 | 2.52 | 2.52 |
| | Leuco Dye | 0.3 | 0.3 | 0.3 |
| | Dimedone | 0.05 | 0.05 | 0.05 |
| | 2,4-di-n-pentylphenol | 3 | 3 | 3 |
| | TX405 | 0.086 | 0.086 | 0.086 |
| | Alkanol XC | 0.27 | 0.27 | 0.27 |
| | Dibasic Sodium Phosphate | 0.028 | 0.028 | 0.028 |
| | Pyridoxal-5-phosphate | 0.11 | 0.11 | 0.11 |
| | Magnesium Chloride Heptahydrate | 0.05 | 0.05 | 0.05 |
| | Cocarboxylase | 0.11 | 0.11 | 0.11 |
| | Flavin Adenine Dinucleotide | 0.011 | 0.011 | 0.011 |
| | Pyruvate Oxidase | 1,000* | 1,000* | 1,000* |
| | Horseradish Peroxidase | 20,000* | 20,000* | 20,000* |
| | Bis(vinylsulfonylmethyl) Ether | 0.16 | 0.16 | 0.156 |
| | pH | 7.5 | 7.5 | 7.5 |

The * means the amounts are U/m². Otherwise they are g/m². The symbols and tradenames in the above and subsequent elements of FIGS. 2–5 have the following meanings:

TX405: Triton X405: An octylphenoxy polyethoxy ethanol nonionic surfactant sold by Rohm and Haas.
Estane: A polyester/polyurethane sold by B. F. Goodrich.
PVPK30: Polyvinylpyrrolidone sold by GAF having a molecular weight of about 40,000. PVPK15 and PVPK90 are the same polymer except having molecular weights of about 10,000 and 360,000 respectively.
TX200: Triton X200: The sodium salt of an alkylaryl polyether sulfonate anionic surfactant sold by Rohm and Haas.
Tricine: N-[Tris(hydroxymethyl)methyl]glycine buffer.
Leuco Dye: 4,5-Bis(4-dimethylaminophenyl)-2-(3,5-dimethoxy- 4-hydroxyphenyl)imidazole.
Alkanol XC: A sodium alkyl naphthalene sulfonate anionic surfactant sold by E. I. dupont de Nemours.
Bis-Tri: Bis(2-hydroxyethyl)iminotris(hydroxymethyl)methane.
Brij 98: Anionic polyoxyethylene oleyl ether surfactant sold by ICI Americas.

The layers shown are coated onto a clear polyester support which has been coated with Uvinul (from BASF) Eastone Orange 2R dye, Eastone Yellow 6 GN dye and Eastone Red R dye to provide a low wavelength light cut-off filter. The Eastone dyes are available from Eastman Fine Chemicals or Eastman Kodak Company.

Analysis of ALT is accomplished by adding an 11 μL sample of serum or plasma containing ALT to the surface of the element. The element is incubated at 37° C. for 5 minutes. Reflectance density measurements are made every 6 sec during the 5-minute incubation. The rate of change of reflectance density with time is calculated over the linear portion of the reflectance density versus time curve. The rate is converted into a concentration by comparison with a calibration curve determined using 3 levels of ALT.

Table I below shows the results of using the elements shown in FIG. 1 for analysis of human serum based fluids containing ALT of various concentrations. All three elements show that ALT concentrations up to at least 992 U/L give measurable and distinct rates. The presence of the hardened gel layers between the subbing layer and the pyruvate oxidase containing layer (Coatings A and B) did not substantially alter the rates obtained for a given ALT concentration.

Table I also notes that physical defects in the spreading layer were noted for the element that did not have a hardened gel interlayer between the subbing layer and the pyruvate oxidase containing layer (Coating C) while the others did not.

TABLE I

| ALT Conc U/L | Rates Coating A | Coating B | Coating C |
|---|---|---|---|
| 9 | 0.0122 | 0.0121 | 0.0156 |
| 20 | 0.0340 | 0.0348 | 0.0348 |
| 43 | 0.0610 | 0.0625 | 0.0584 |
| 60 | 0.0824 | 0.0851 | 0.0792 |
| 99 | 0.1201 | 0.1234 | 0.1169 |
| 405 | 0.3252 | 0.3171 | 0.2733 |
| 715 | 0.4071 | 0.3808 | 0.3611 |
| 992 | 0.4408 | 0.4025 | 0.4072 |
| Defects? | No | No | Yes |

Example 2

FIG. 2 shows the configuration and composition of an alternate multiple thin-layer element for analysis of ALT which was coated onto a clear polyester support coated with dyes as in example 1 to give a low wavelength cut-off filter.

FIG. 2

| | | Coating D g/or U/m²* |
|---|---|---|
| Spreading Layer | Sodium a-Ketoglutarate | 0.54 |
| | Alanine | 8.61 |
| | Barium Sulfate | 93.08 |
| | Cellulose Acetate | 7.87 |
| | Hexadecyl Pyridinium Bromide | 1.07 |
| | TX405 | 1.85 |
| | Estane | 0.93 |
| Subbing Layer | PVPK30 | 1.07 |
| Gelatin Layer | Gelatin | 8.22 |
| | Tricine | 1.08 |
| | TX200 | 0.15 |
| | Dibasic Sodium Phosphate | 0.218 |
| | Bis(vinylsulfonylmethyl) Ether | 0.16 |
| | Pyridoxal-5-phosphate | 0.11 |
| | Magnesium Chloride Heptahydrate | 0.05 |
| | Flavin Adenine Dinucleotide | 0.011 |
| | Cocarboxylase | 0.11 |
| | Pyruvate Oxidase | 1,000* |
| | pH | 7.5 |
| Reagent Layer | Gelatin | 6 |
| | Tricine | 1.66 |
| | TX200 | 0.11 |
| | Alkanol XC | 0.27 |
| | 2,4-di-n-pentylphenol | 1.35 |
| | Dimedone | 0.05 |
| | Leuco Dye | 0.19 |
| | Bis-Tris | 0.11 |
| | Horseradish Peroxidase | 21,520* |
| | pH | 7.5 |

Analysis for ALT was accomplished as described in Example 1. Table II shows the rate of change of reflectance density with time for ALT concentrations ranging from 9 to 992 U/L. Again, measurable and distinct rates are obtained for ALT concentrations throughout this range indicating this element can also be used for analysis of ALT.

TABLE II

| ALT Conc U/L | Rates Coating D |
|---|---|
| 9 | 0.0077 |
| 20 | 0.0205 |
| 43 | 0.0269 |
| 60 | 0.0316 |
| 99 | 0.0368 |
| 405 | 0.0543 |
| 715 | 0.0940 |
| 992 | 0.1718 |
| Defects? | No |

Example 3

FIG. 3 shows the configurations and compositions of multiple thin-layer elements for analysis of ALT which were coated onto clear polyester support coated with dyes to give a low wavelength cut-off filter as in Example 1.

FIG. 3

|  |  | Coating E g/or U/m²* | Coating F g/or U/m²* | Coating G g/or U/m²* | Coating H g/or U/m²* |
|---|---|---|---|---|---|
| Spread Layer | Sodium a-Ketoglutarate | 0.54 | 0.54 | 0.54 | 0.54 |
|  | Alanine | 8.61 | 8.61 | 8.61 | 8.61 |
|  | Barium Sulfate | 93.08 | 93.08 | 93.08 | 93.08 |
|  | Cellulose Acetate | 7.87 | 7.87 | 7.87 | 7.87 |
|  | Hexadecyl Pyridinium Bromide | 1.07 | 1.07 | 1.07 | 1.07 |
|  | TX405 | 1.85 | 1.85 | 1.85 | 1.85 |
|  | Estane | 0.93 | 0.93 | 0.93 | 0.93 |
| Subbing Layer | PVPK30 | 1.07 | 1.07 | 0 | 0 |
|  | PVPK15 | 0 | 0 | 2.14 | 0 |
|  | PVPK90 | 0 | 0 | 0 | 2.14 |
| Gelatin Layer | Gelatin | 0 | 3 | 0 | 0 |
|  | Sodium Hydroxide | 0 | 0.0171 | 0 | 0 |
|  | TX405 | 0 | 0.014 | 0 | 0 |
|  | Bis(vinylsulfonyl-methyl) Ether | 0 | 0.06 | 0 | 0 |
| Reagent Layer | Gelatin | 8.22 | 8.22 | 8.22 | 8.22 |
|  | Tricine | 5.84 | 5.84 | 5.84 | 5.84 |
|  | Leuco Dye | 0.3 | 0.3 | 0.3 | 0.3 |
|  | Dimedone | 0.05 | 0.05 | 0.05 | 0.05 |
|  | 2,4-di-n-pentylphenol | 3 | 3 | 3 | 3 |
|  | TX405 | 0.082 | 0.082 | 0.082 | 0.082 |
|  | Alkanol XC | 0.27 | 0.27 | 0.27 | 0.27 |
|  | Dibasic Sodium Phosphate | 0.028 | 0.028 | 0.028 | 0.028 |
|  | Pyridoxal-5-phosphate | 0.11 | 0.11 | 0.11 | 0.11 |
|  | Magnesium Chloride Heptahydrate | 0.05 | 0.05 | 0.05 | 0.05 |
|  | Cocarboxylase | 0.11 | 0.11 | 0.11 | 0.11 |
|  | Flavin Adenine Dinucleotide | 0.011 | 0.011 | 0.011 | 0.011 |
|  | Pyruvate Oxidase | 1,000* | 1,000* | 1,000* | 1,000* |
|  | 4'-Hydroxyacetanilide | 0.0454 | 0.0454 | 0.0454 | 0.0454 |
|  | Horseradish Peroxidase | 2,000* | 2,000* | 2,000* | 2,000* |
|  | Bis(vinylsulfonyl-methyl) Ether | 0.16 | 0.16 | 0.16 | 0.16 |
|  | TX200 | 0.004 | 0.004 | 0.004 | 0.004 |
|  | pH | 7.5 | 7.5 | 7.5 | 7.5 |

The fluids measured were control fluids manufactured by Kodak containing ALT. The ALT concentrations were calculated by comparison of the rate of reflectance density change with time with a calibration curve generated with 3 calibrating fluids. The standard deviation of the measurement based on 25 replicates was calculated. The coefficients of variation (standard deviation/mean concentration) are shown in Table III for the two fluids.

TABLE III

| | % Coefficient of Variation, n = 25 | | | |
|---|---|---|---|---|
| Fluid | Coating E | Coating F | Coating G | Coating H |
| Kodatrol 1 | 4.31 | 2.27 | 6.51 | 3.78 |
| Kodatrol 2 | 5.47 | 1.62 | 4.73 | 4.41 |
| Defects? | Yes | No | No | No |

Coating F, which contained a hardened gel layer between the subbing layer and the pyruvate oxidase layer, gave substantially lower coefficient of variations for both control fluids compared with the control Coating E. In addition, Coating F did not have physical defects in the spreading layer as seen with Coating E.

Coatings G and H, which contain a higher amount of subbing polymer than the control Coating E, also show lower coefficients of variation for one or both control fluids. Coatings G and H also did not show physical defects in the spreading layer.

These coatings show that increasing dry coverages of the subbing layer eliminates the coating defects and improves precision of at least the high level control fluid. Using a hardened gel layer eliminates the coating defects and improves precision. Neither the addition of the hardened gel layer or increased coverage of the subbing layer polymer required increase in the pyruvate oxidase in the reagent layer to obtain these results.

Example 4

FIG. 4 shows the configuration and composition of a multiple thin-layer element for the measurement of aspartate aminotransferase (AST) coated onto clear polyester coated with dyes to provide a low wavelength cut-off filter as in example 1.

FIG. 4

| | | Coating I g/or U/m²* |
|---|---|---|
| Spreading Layer | Sodium a-Ketoglutarate | 1.28 |
| | Sodium Aspartate | 2.69 |
| | Barium Sulfate | 93.08 |

-continued
FIG. 4

|  |  | Coating I g/or U/m²* |
|---|---|---|
| Subbing Layer | Cellulose Acetate | 7.87 |
|  | Hexadecyl Pyridinium Bromide | 1.07 |
|  | TX405 | 1.85 |
|  | Estane | 0.93 |
|  | PVPK30 | 1.07 |
| Gelatin Layer | Gelatin | 3 |
|  | Sodium Hydroxide | 0.0169 |
|  | TX405 | 0.01 |
|  | Bis(vinylsulfonylmethyl) Ether | 0.06 |
|  | TX200 | 0.004 |
| Reagent Layer | Gelatin | 8.22 |
|  | Tricine | 5.84 |
|  | Leuco Dye | 0.3 |
|  | Dimedone | 0.05 |
|  | 2,4-di-t-pentylphenol | 3 |
|  | TX405 | 0.127 |
|  | Alkanol XC | 0.243 |
|  | Dibasic Sodium Phosphate | 0.42 |
|  | Pyridoxal-5-phosphate | 0.16 |
|  | Magnesium Chloride Heptahydrate | 0.05 |
|  | Flavin Adenine Dinucleotide | 0.0124 |
|  | Cocarboxylase | 0.11 |
|  | Pyruvate Oxidase | 2,000* |
|  | 4'-Hydroxyacetanilide | 0.0454 |
|  | Horseradish Peroxidase | 10,000* |
|  | Ascorbic Acid Oxidase | 3,500* |
|  | Oxaloacetate Decarboxylase | 3,000* |
|  | Bis(vinylsulfonylmethyl) Ether | 0.16 |
|  | pH | 7.5 |

Analysis of AST was accomplished as described in Example 1. Table IV shows the rate of reflectance change as a function of time for human serum based fluids containing AST in concentrations from 3.5 to 893.8 U/L. The results indicate that the rates are measurable and distinct over the concentration range measured.

TABLE IV

| AST Conc U/L | Rates Coating I |
|---|---|
| 3.5 | 0.0034 |
| 28.1 | 0.0484 |
| 66.7 | 0.0990 |
| 525.5 | 0.5000 |
| 763.2 | 0.6191 |
| 893.8 | 0.7015 |

Example 5

FIG. 5 shows the configuration and composition of a multiple thin-layer element for measurement of ALT utilizing a TiO₂ spreading layer coated onto polyester coated with dyes to give a low wavelength cut-off filter as in Example 1.

FIG. 5

|  |  | Coating J g or U/m²* |
|---|---|---|
| Spreading Layer | Sodium a-Ketoglutarate | 0.54 |
|  | Alanine | 8.601 |
|  | Titanium Dioxide | 50.32 |
|  | Cellulose Acetate | 7.32 |
|  | Brij 98 | 0.832 |

-continued
FIG. 5

|  |  | Coating J g or U/m²* |
|---|---|---|
| Subbing Layer | TX405 | 1.656 |
|  | Estane | 0.93 |
|  | PVPK30 | 1.07 |
| Gelatin Layer | Gelatin | 8.22 |
|  | Tricine | 1.08 |
|  | TX200 | 0.114 |
|  | Dibasic Sodium Phosphate | 0.218 |
|  | Pyridoxal-5-phosphate | 0.11 |
|  | Magnesium Chloride Heptahydrate | 0.05 |
|  | Flavin Adenine Dinucleotide | 0.011 |
|  | Cocarboxylase | 0.11 |
|  | Pyruvate Oxidase | 770* |
|  | Bis(vinylsulfonylmethyl) Ether | 0.16 |
|  | pH | 7.5 |
| Reagent Layer | Gelatin | 6 |
|  | Tricine | 1.66 |
|  | TX200 | 0.11 |
|  | Alkanol XC | 0.27 |
|  | 2,4-di-n-pentylphenol | 1.35 |
|  | Dimedone | 0.05 |
|  | Leuco Dye | 0.19 |
|  | Bis(vinylsulfonylmethyl) Ether | 0.144 |
|  | TX405 | 0.006 |
|  | Bis-Tris | 0.11 |
|  | Horseradish Peroxidase | 21,520* |
|  | pH | 7.5 |

Analysis of ALT was accomplished as described in Example 1, except that the maximum rate was calculated graphically from the curve of $dD_r/d_t$ versus time.

Table V shows the rate of reflectance change as a function of time for calibrator fluids containing ALT concentrations from 34 to 864 U/L. The results indicate that this element can measure ALT throughout this concentration range.

TABLE V

| ALT Conc, U/L | Vmax, Dr/min |
|---|---|
| 34 | 0.02 |
| 225 | 0.07 |
| 864 | 0.27 |

The invention has been described in detail with particular reference to preferred embodiments thereof, but it will be understood that variations and modifications can be effected within the spirit and scope of the invention.

We claim:

1. A dry multilayer analytical element for assaying transaminases wherein said element comprises:
   a) a transaminase substrate;
   b) reagents that generate pyruvate in the presence of a transaminase and the transaminase substrate;
   c) pyruvate oxidase and cofactors for pyruvate oxidase; and
   d) reagents that generate a color in proportion to a concentration of hydrogen peroxide;
   and wherein said element has, in the following order, a spreading layer, a reagent layer, and a support wherein
      i) the spreading layer contains the transaminase substrate and a material selected from the group consisting of polymer beads, barium sulfate, titanium oxide, and mixtures thereof;
      ii) the reagent layer contains the pyruvate oxidase; and
      iii) both a hardened gelatin layer and a subbing layer separate the reagent layer from the spreading layer.

2. The element of claim 1 wherein the subbing layer comprises polyvinylpyrrolidone.

3. The element of claim 2 wherein the polyvinylpyrrolidone has molecular weight of 10,000 to 360,000.

4. The element of claim 3 wherein the polyvinylpyrrolidone has molecular weight of about 40,000.

5. The element of claim 1 or 4 wherein the reagent layer comprises from about 1000 to 4500 U/m$^2$ of pyruvate oxidase.

6. The element of claim 1 or 4 wherein the reagents that generate a color in proportion to the concentration of hydrogen peroxide are a leuco dye and horseradish peroxidase;

7. A dry multilayer analytical element for assaying aspartate aminotransaminase wherein said element comprises:
 a) aspartate;
 b) reagents that generate pyruvate in the presence of aspartate aminotransaminase and aspartate;
 c) pyruvate oxidase and cofactors for pyruvate oxidase; and
 d) reagents that generate a color in proportion to a concentration of hydrogen peroxide;
and wherein said element has, in the following order, a spreading layer, a reagent layer, and a support wherein
 i) the spreading layer contains aspartate and a material selected from the group consisting of polymer beads, barium sulfate, titanium oxide, and mixtures thereof;
 ii) the reagent layer contains the pyruvate oxidase; and
 iii) both a hardened gelatin layer and a subbing layer separate the reagent layer from the spreading layer.

8. A dry multilayer analytical element for assaying alanine aminotransaminase wherein said element comprises:
 a) alanine;
 b) reagents that generate pyruvate in the presence of alanine aminotransaminase and alanine;
 c) pyruvate oxidase and cofactors for pyruvate oxidase; and
 d) reagents that generate a color in proportion to a concentration of hydrogen peroxide;
and wherein said element has, in the following order, a spreading layer, a reagent layer, and a support wherein
 i) the spreading layer contains alanine and a material selected from the group consisting of polymer beads, barium sulfate, titanium oxide, and mixtures thereof;
 ii) the reagent layer contains the pyruvate oxidase; and
 iii) both a hardened gelatin layer and a subbing layer separate the reagent layer from the spreading layer.

9. The element of claim 7 or 8 wherein the subbing layer is polyvinylpyrrolidone.

10. The element of claim 9 wherein the polyvinylpyrrolidone has a molecular weight of 10,000 to 360,000.

11. The element of claim 10 wherein the polyvinylpyrrolidone has a molecular weight of about 40,000.

12. The element of claim 7 or 8 wherein the reagent layer comprises from about 1000 to 4500 U/m$^2$ of pyruvate oxidase.

13. The element of claim 7 or 8 wherein the reagents that generate a color in proportion to the concentration of hydrogen peroxide are a leuco dye and horseradish peroxidase.

14. An element according to claim 1, 7 or 8 wherein the spreading layer comprises barium sulfate or titanium dioxide.

* * * * *